United States Patent [19]

Liberman et al.

[11] Patent Number: 4,650,795
[45] Date of Patent: Mar. 17, 1987

[54] AMINE SALTS OF CLAVULANIC ACID AS ANTIBACTERIAL AGENTS

[75] Inventors: Michael Liberman, Redhill; Kenneth T. Veal, Uckfield, both of England

[73] Assignee: Beecham Group p.l.c., England

[21] Appl. No.: 791,907

[22] Filed: Oct. 28, 1985

Related U.S. Application Data

[63] Continuation of Ser. No. 417,990, Sep. 14, 1982, abandoned, which is a continuation of Ser. No. 8,429, Feb. 1, 1979, abandoned, which is a continuation of Ser. No. 815,564, Jul. 14, 1977, abandoned.

[30] Foreign Application Priority Data

Jul. 23, 1976 [GB] United Kingdom ............... 30752/76

[51] Int. Cl.$^4$ ..................... C07D 487/04; A61K 31/42
[52] U.S. Cl. ..................................... 514/210; 540/349
[58] Field of Search ....................... 260/245.3; 514/210

[56] References Cited

U.S. PATENT DOCUMENTS 4,060,530 11/1977 Howarth ........................... 260/245.3

Primary Examiner—Mark L. Berch
Attorney, Agent, or Firm—Jacobs & Jacobs

[57] ABSTRACT

The present invention provides the salts of the formula (II):

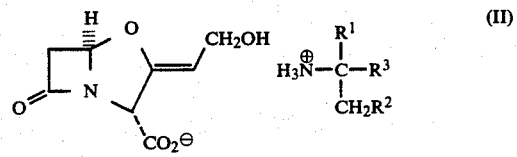

wherein $R^1$ is a hydrogen atom or a lower alkyl, aralkyl, phenyl or inertly substituted lower alkyl, aralkyl or phenyl group; $R^2$ is a hydrogen atom or a lower alkyl, aralkyl, phenyl or inertly substituted lower alkyl, aralkyl or phenyl group; and $R^3$ is lower alkyl, aralkyl, phenyl or inertly substituted lower alkyl, aralkyl or phenyl group; any of said groups $R^1$, $R^2$ and $R^3$ being optionally interlinked to form a ring of 5–7 ring atoms. The compounds are antibacterials.

11 Claims, No Drawings

AMINE SALTS OF CLAVULANIC ACID AS ANTIBACTERIAL AGENTS

CROSS-REFERENCE

This is a continuation of Ser. No. 417,990 filed Sept. 14, 1982, which is a continuation of Ser. No. 008,429 filed Feb. 1, 1979, which is a continuation of Ser. No. 815,564 filed July 14, 1977 abandoned.

The present invention relates to salts of clavulanic acid, to their preparation and to compositions containing them.

Belgian Pat. No. 827926 discloses inter alia that clavulanic acid, which has the formula (I):

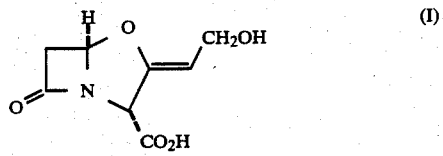

and its pharmaceutically acceptable salts are antibacterial agents which are able to enhance the effectiveness of penicillins and cephalosporins against many $\beta$-lactamase producing bacteria. There has now been discovered a class of salts of clavulanic acid which are more easily formulated to give stable pharmaceutical compositions than are the previously described salts such as the sodium or potassium slats of clavulanic acid.

Accordingly the present invention provides the salts of the formula (II):

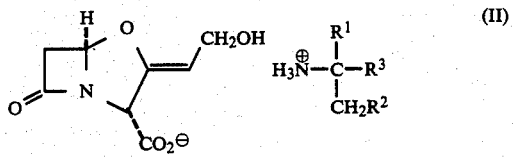

wherein $R^1$ is a hydrogen atom or a lower alkyl, aralkyl, phenyl or inertly substituted lower alkyl, aralkyl or phenyl group; $R^2$ is a hydrogen atom or a lower alkyl, aralkyl, phenyl or inertly substituted lower alkyl, aralkyl or phenyl group; and $R^3$ is lower alkyl, aralkyl, phenyl or inertly substituted lower alkyl, aralkyl or phenyl group; any of said groups $R^1$, $R^2$ and $R^3$ being optionally interlinked to form a ring of 5-7 ring atoms.

When used herein the term 'lower' means that the group contains up to 6 carbon atoms. When used herein the term 'aralkyl' means a lower alkyl group substituted by a phenyl or inertly substituted phenyl group.

Suitable inert substituents include halogen, lower alkoxyl, lower acyloxyl, lower esterified carboxyl and the like groups. Suitably 1, 2 or 3 such substituent groups are present, more suitably 1 or 2 and preferably not more than one such substituent group is present.

Normally and preferably the amine of the formula (III):

from which the salt of the formula (II) is notionally derivable is a pharmaceutically acceptable amine.

Most suitably $R^1$ is a lower alkyl group; most suitably $R^2$ is a hydrogen atom or a lower alkyl group; most suitably $R^3$ is a lower alkyl or aralkyl group; any of said groups being linked to form a 5-7 membered ring.

Most suitably the compound of the formula (III) does not contain a chiral centre.

Suitably the salt of the formula (II) is notionally derivable from an amine of the formula (III) which contains 4-16 carbon atoms, more suitably 4-12 carbon atoms and preferably 4-10 carbon atoms.

Suitably the salt of the formula (II) is notionally derivable from 2-amino-2-methylpropane, 2-amino-2-methylbutane, 2-amino-2-methylpentane, 2-amino-2-methylhexane, 2-amino-2-methylheptane, 2-amino-2-methyloctane, 3-amino-3-methylpentane, 1-amino-1-methylcyclohexane, 1-aminospiro-adamantane and other similar amines.

Preferred salts of the formula (II) are crystalline.

The present invention also provides a process for the preparation of the salts of formula (II) which process comprises the reaction of clavulanic acid with an amine of the formula (III).

Most suitably this reaction takes place in an organic solvent. Suitable solvents include such conventional nonhydroxylic solvents as tetrahydrofuran, dioxane, ethyl acetate, methyl acetate, acetone, methylethylketone and the like solvent.

The salt forming reaction may take place at any nonextreme temperature but in general temperatures of from 0° C. to 35° C. are most suitable and temperatures of from 5° C. to 25° C. are generally most convenient.

The salt of the formula (II) may be recovered from the solution in conventional manner such as evaporation of the solvent under reduced pressure or preferably by crystallisation.

It is frequently convenient to prepare the clavulanic acid in situ, for example by hydrogenation of the benzyl or chemically equivalent ester.

The present invention also provides a process for the preparation of a salt of the formula (II) which process comprises the displacement of an alternative cation from an alternative salt of clavulanic acid by a protonated amine of the formula (III).

The present invention also provides pharmaceutical compositions which comprise a salt of the formula (II) and a pharmaceutically acceptable carrier.

Suitable forms of the compositions of this invention will be similar to those described in Belgian Pat. No. 827926 as suitable for salts of clavulanic acid.

Particularly suitable forms of the compositions of this invention are those which do not contain high levels of residual water. Most suitably such compositions are prepared from dry materials so that the final compositions contain less than 5% moisture, more suitably less than 3% moisture and preferably less than 2% moisture, for example 1% or less of moisture.

Most suitably the compositions of this invention are packaged in moisture-excluding forms such as closed containers, foil lined packs and the like.

The compositions of the invention include those in a form adapted for oral, topical or parenteral use and may be used for the treatment of infection in mammals including humans.

Suitable forms of the compositions of this invention include tablets, capsules, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Injectable or infusable compositions of the salts of formula (II) are particularly suitable as high tissue levels of the compound of clavulanic acid can occur after administration by injection or infusion. Thus, one preferred composition aspect of this invention comprises a salt of the formula (II) in sterile form.

Unit dose compositions comprising a salt of the formula (II) adapted for oral administration form a further preferred composition aspect of this invention.

Suitable β-lactam antibiotics for inclusion in such synergistic compositions containing a salt of the formula (II) include not only those known to be highly susceptible to β-lactamases but also those which have a good degree of intrinsic resistance to β-lactamases. Thus, suitable β-lactam antibiotics for inclusion in the compositions of this invention include benzylpenicillin, phenoxymethylpenicillin, carbenicillin, methicillin, propicillin, ampicillin, amoxycillin, epicillin, ticarcillin, cyclacillin, pirbenicillin, cephatriazine, cephaloridine, cephalothin, cefazolin, cephalexin, cefoxitin, cephacetrile, cephamandole, cephapirin, cephradine, cephaloglycine and other well known penicillins and cephalosporins or pro-drugs therefor such as hetacillin, metampicillin, the acetoxymethyl, pivaloyloxymethyl or phthalidyl esters of benzylpenicillin, ampicillin, amoxycillin or cephaloglycine or the phenyl, tolyl or indanyl α-esters of carbenicillin or ticarcillin or the like.

Naturally if the penicillin or cephalosporin present in the composition is not suitable for oral administration then the composition will be adapted for parenteral administration.

When present in a pharmaceutical composition together with a β-lactam antibiotic, the ratio of the salt of formula (II) present to β-lactam antibiotic present may be from, for example, 3:1 to 1:10 and advantageously may be from 1:1 to 1:6, for example from 1:3 to 1:5.

The total quantity of antibacterial agents present in any unit dosage form will normally be between 50 and 1500 mg and will usually be between 100 and 1000 mg.

Compositions of this invention may be used for the treatment of infections of inter alia, the respiratory tract, the urinary tract and soft tissues in humans.

Compositions of this invention may also be used to treat infections of domestic animals such as mastitis in cattle.

Normally between 50 and 6000 mg of the compositions of the invention will be administered each day of treatment but more usually between 500 and 300 mg of the composition of the invention will be administered per day.

Particularly favoured compositions of this invention will contain from 150–1000 mg of amoxycillin, ampicillin or a pro-drug therefor and from 50–500 mg of a salt of the formula (II) and more suitably from 200–500 mg of amoxycillin, ampicillin or a pro-drug therefor and from 50–250 mg of a salt of the formula (II).

Most suitably such compositions comprise amoxycillin trihydrate.

The following Examples illustrate the invention:

EXAMPLE 1

Clavulanic acid 2-amino-2,4,4-trimethylpentane salt

Benzyl clavulanate (purified by Sephadex chromatography, 20 g, 0.07 moles) was dissolved in tetrahydrofuran (distilled from calcium hydride, 400 ml) and 10% palladium on charcoal catalyst (5.7 g) added. The mixture was hydrogenated with stirring at ambient temperature and about 15 psi for 20–30 minutes. The state of reaction was judged by thin layer chromatography using silica plates developed with ethyl acetate and visualised using triphenyltetrazolium chloride spray reagent. Clavulanic acid Rf 0.0, benzyl ester 0.4.

The reaction mixture was filtered and the filter pad well washed. The combined filtrates (500 ml) containing clavulanic acid were treated with stirring with 2-amino-2,4,4-trimethylpentane (9.0 g, 0.07 moles) in dry tetrahydrofuran (50 ml). Crystallisation was observed within one minute. The mixture was stirred for 0.5 hours at ambient temperature and then 2 hours at 5°. The product was filtered off, washed with dry tetrahydrofuran (100 ml) and dried in vacuo for 12 hours to afford 23.0 g, 100% of the title salt, having m.p. 160°–170° (d).

EXAMPLE 2

Clavulanic acid 1-aminoadamantane salt

Benzyl clavulanate (3.5 g, 0.012 mole) was hydrogenolysed in tetrahydrofuran (70 ml) as described above. The filtrate plus washings (total 100 ml) was treated with stirring with a solution of 1-aminoadamantane (1.82 g, 0.012 moles) in dry tetrahydrofuran (25 ml) at ambient temperature. Crystallization was rapid. The suspension was stirred at ambient temperature for 0.5 hours, at 5° for two hours and then filtered. The solid was washed and dried as described above to give 3.5 g, 83% yield of the title salt, having m.p. 190–192 (d) with the following elemental analysis results:

Requires: C, 61.70; H, 7.48; N, 7.99%. Found: C, 61.40; H, 7.31; N, 7.77%.

EXAMPLE 3

Clavulanic acid 2-amino-2-methylpropane salt

The preparation was carried out as in Example 1 using benzyl clavulanate (0.9 g, 0.003 moles) and treating the resulting clavulanic acid solution with 2-amino-2-methylpropane (0.22 g, 0.003 mole) in dry tetrahydrofuran (10 ml). The title salt 0.6 g, 73% yield, had m.p. 150°–152° (d).

EXAMPLE 4

Clavulanic acid D(+) 1-methylbenzylamine salt

The preparation was carried out as in Example 1 using benzyl clavulanate (0.9 g, 0.003 moles) and treating the resulting clavulanic acid solution with D(+) 1-methylbenzylamine in dry tetrahydrofuran (10 ml). The mixture was stored at 50° for two days during which time a slow crystallization occurred. Filtration afforded the title salt 0.6 g, 62% yield, having m.p. 125° (d).

EXAMPLE 5

Hard gelatin capsules may be filled with 50 mg of a compound of any of Examples 1–4.

EXAMPLE 6

Hard gelatin capsules may be filled with a mixture consisting essentially of 50 mg of a coupound of any of Examples 1-4 and 250 mg of amoxycillin trihydrate.

EXAMPLE 7

When stored for 72 hours at ambient temperature under conditions of 50% humidity the products of Examples 1-7 were found to absorb considerably less moisture than sodium clavulanate or potassium clavulanate maintained under the same conditions. In accelerated storage tests under conditions of 50% humidity the compounds of Examples 1-4 may be shown to be more stable than sodium clavulanate tetrahydrate.

What we claim is:

1. A pharmaceutically acceptable salt of the formula:

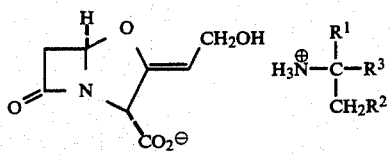

wherein $R^1$ is hydrogen, alkyl of up to 6 carbon atoms; $R^2$ is hydrogen, alkyl of up to 6 carbon atoms, alkyl of up to 6 carbon atoms substituted by phenyl which is itself unsubstituted or substituted by 1, 2 or 3 substituents selected from the group consisting of halogen, alkoxyl of up to 6 carbon atoms and acyloxyl of up to 6 carbon atoms, phenyl, alkyl of up to 6 carbon atoms substituted by 1, 2 or 3 substituents selected from the group consisting of halogen, alkoxyl of up to 6 carbon atoms and acyloxyl of up to 6 carbon atoms, or phenyl substituted by 1, 2 or 3 substituents selected from the group consisting of halogen, alkoxyl of up to 6 carbon atoms and acyloxyl of up to 6 carbon atoms; and $R^3$ is alkyl of up to 6 carbon atoms, alkyl of up to 6 carbon atoms substituted by phenyl which is itself unsubstituted or substituted by 1, 2 or 3 substituents selected from the group consisting of halogen, alkoxyl of up to 6 carbon atoms and acyloxyl of up to 6 carbon atoms, phenyl, alkyl of up to 6 carbon atoms substituted by 1, 2 or 3 substituents selected from the group consisting of halogen, alkoxyl of up to 6 carbon atoms and acyloxyl of up to 6 carbon atoms, or phenyl substituted by 1, 2 or 3 substituents selected from the group consisting of halogen, alkoxyl of up to 6 carbon atoms and acyloxyl of up to 6 carbon atoms; or any of said groups $R^1$, $R^2$ and $R^3$ are interlinked to form a ring of 5 to 7 ring atoms, or $R^1$, $R^2$ and $R^3$ are interlinked to form an adamantane ring.

2. A salt according to claim 1 wherein $R^2$ is hydrogen or alkyl of up to 6 carbon atoms.

3. A salt according to claim 1 wherein $R^3$ is alkyl of up to 6 carbon atoms unsubstituted or substituted by phenyl, which is itself unsubstituted or substituted by phenyl, which is itself unsubstituted or substituted by 1, 2 or 3 substituents selected from the group consisting of halogen, alkoxyl of up to 6 carbon atoms and acyloxyl of up to 6 carbon atoms.

4. A salt according to claim 1 wherein the amine contains a total of from 4 to 16 carbon atoms.

5. A salt according to claim 1 wherein the salt is the 2-amino-2-methylpropane, 2-amino-2-methylbutane, 2-amino-2-methylpentane, 2-amino-2-methylhexane, 2-amino-2-methylheptane, 2-amino-2-methyloctane, 3-amino-3-methylpentane, 1-amino-1-methylcyclohexane, 2-amino-2,4,4-trimethylpentane, D(+)1-methyl-benzylamine or 1-amino-adamantane salt of clavulanic acid.

6. A salt according to claim 1 wherein $R^1$ is alkyl of up to 6 carbon atoms; $R^2$ is hydrogen, alkyl of up to 6 carbon atoms, alkyl of up to 6 carbon atoms substituted by phenyl which is itself unsubstituted or substituted by one or two substituents selected from the group consisting of halogen, alkoxyl of up to 6 carbon atoms and acyloxyl of up to 6 carbon atoms, phenyl, alkyl of up to 6 carbon atoms substituted by one or two substituents selected from the group consisting of halogen, alkoxyl of up to 6 carbon atoms and acyloxyl of up to 6 carbon atoms, or phenyl substituted by one or two substituents selected from the group consisting of halogen, alkoxyl of up to 6 carbon atoms and acyloxyl of up to 6 carbon atoms; and $R^3$ is alkyl of up to 6 carbon atoms unsubstituted or substituted by one or two substituents selected from the group consisting of halogen, alkoxy of up to 6 carbon atoms and acyloxyl of up to 6 carbon atoms, phenyl, alkyl of up to 6 carbon atoms substituted by one or two substituents selected from the group consisting of halogen, alkoxy of up to 6 carbon atoms and alkoxyl of up to 6 carbon atoms, or phenyl substituted by one or two substituents selected from the group consisting of halogen, alkoxyl of up to 6 carbon atoms and acyloxyl of up to 6 carbon atoms; or any of said groups $R^1$, $R^2$ and $R^3$ are interlinked to form a ring of 5 to 7 ring atoms, or $R^1$, $R^2$ and $R^3$ are interlinked to form an adamantane ring.

7. A salt according to claim 1 wherein $R^1$ is alkyl of up to 6 carbon atoms; $R^2$ is halogen, alkyl of up to 6 carbon atoms, alkyl of up to 6 carbon atoms substituted by phenyl which is itself unsubstituted or substituted by a substituent selected from the group consisting of halogen, alkoxyl of up to 6 carbon atoms and acyloxyl of up to 6 carbon atoms, phenyl, alkyl of up to 6 carbon atoms substituted by a substituent selected from the group consisting of halogen, alkoxyl of up to 6 carbon atoms and acyloxyl of up to 6 carbon atoms, or phenyl substituted by a substituent selected from the group consisting of halogen, alkoxyl of up to 6 carbon atoms and acyloxyl of up to 6 carbon atoms; and $R^3$ is alkyl of up to 6 carbon atoms, alkyl of up to 6 carbon atoms substituted by a substituent selected from the group consisting of halogen, alkoxyl of up to 6 carbon atoms and acyloxyl of up to 6 carbon atoms, phenyl, alkyl of up to 6 carbon atoms substituted by a substituent selected from the group consisting of halogen, alkoxyl of up to 6 carbon atoms and acyloxyl of up to 6 carbon atoms, or phenyl substituted by a substituent selected from the group consisting of halogen, alkoxyl of up to 6 carbon atoms and acyloxyl of up to 6 carbon atoms; or any of said groups $R^1$, $R^2$ and $R^3$ are interlinked to form a ring of 5 to 7 ring atoms; or $R^1$, $R^2$ and $R^3$ are interlinked to form an adamantane ring.

8. A salt according to claim 1 wherein $R^1$ is alkyl of up to 6 carbon atoms; $R^2$ is hydrogen or alkyl of up to 6 carbon atoms; and $R^3$ is alkyl of up to 6 carbon atoms or alkyl of up to 6 carbon atoms substituted by phenyl which itself is unsubstituted or substituted by a substituent selected from the group consisting of halogen, alkoxyl of up to 6 carbon atoms or acyloxyl of up to 6 carbon atoms; or any of said groups $R^1$, $R^2$ and $R^3$ are interlinked to form a ring of 5 to 7 ring atoms; or $R^1$, $R^2$ and $R^3$ are interlinked to form an adamantane ring.

9. A salt according to claim 4 wherein the amine contains a total of 4 to 12 carbon atoms.

10. A salt according to claim 4 wherein the amine contains a total of 4 to 10 carbon atoms.

11. A salt according to claim 1 which is in crystalline form.

* * * * *